(12) United States Patent
Bishop et al.

(10) Patent No.: US 6,242,434 B1
(45) Date of Patent: Jun. 5, 2001

(54) 24-HYDROXYVITAMIN D, ANALOGS AND USES THEREOF

(75) Inventors: Charles W. Bishop; Joyce C. Knutson; Stephen Strugnell, all of Madison, WI (US)

(73) Assignee: Bone Care International, Inc., Madison, WI (US)

( * ) Notice: Subject to any disclaimer, the term of this patent is extended or adjusted under 35 U.S.C. 154(b) by 0 days.

(21) Appl. No.: 09/086,969

(22) Filed: May 29, 1998

Related U.S. Application Data

(63) Continuation-in-part of application No. 08/907,659, filed on Aug. 8, 1997, now Pat. No. 5,869,473.

(51) Int. Cl.$^7$ .................................................. A61K 31/59
(52) U.S. Cl. .......................................................... 514/167
(58) Field of Search .............................. 514/167; 552/653

(56) References Cited

U.S. PATENT DOCUMENTS

| | | | |
|---|---|---|---|
| 3,907,843 | 9/1975 | DeLuca et al. | 260/397.2 |
| 4,195,027 | 3/1980 | DeLuca et al. | 260/397.2 |
| 4,202,829 | 5/1980 | DeLuca et al. | 260/397.2 |
| 4,225,596 | 9/1980 | DeLuca | 424/236 |
| 4,234,495 | 11/1980 | DeLuca et al. | 260/397.2 |
| 4,260,549 | 4/1981 | DeLuca et al. | 260/397.2 |
| 4,341,774 | 7/1982 | Aoki et al. | 260/397.2 |
| 4,388,243 | 6/1983 | Nishikawa et al. | 260/397.2 |
| 4,391,802 | 7/1983 | Suda et al. | 424/236 |
| 4,554,106 | 11/1998 | DeLuca et al. | 260/397.2 |
| 4,555,364 | 11/1985 | DeLuca et al. | 260/397.2 |
| 4,652,405 | 3/1987 | Partridge et al. | 260/397.1 |
| 4,689,180 | 8/1987 | DeLuca et al. | 260/397.2 |
| 4,698,328 | 10/1987 | Neer et al. | 514/12 |
| 4,749,710 | 6/1988 | Truitt et al. | 514/167 |
| 4,833,125 | 5/1989 | Neer et al. | 514/12 |
| 4,866,048 | * 9/1989 | Calverley et al. | 514/167 |
| 4,891,364 | 1/1990 | Kubodera et al. | 514/167 |
| 4,897,388 | 1/1990 | Malluche | 514/167 |
| 5,035,783 | 7/1991 | Goethals et al. | 204/157.67 |
| 5,063,221 | * 11/1991 | Nishii et al. | 514/167 |
| 5,098,899 | 3/1992 | Gilbert et al. | 514/167 |
| 5,190,935 | 3/1993 | Binderup et al. | 514/167 |
| 5,206,229 | 4/1993 | Calverley et al. | 514/167 |
| 5,250,523 | 10/1993 | DeLuca et al. | 514/167 |
| 5,252,191 | 10/1993 | Pauli et al. | 204/157.67 |
| 5,304,291 | 4/1994 | Bout et al. | 204/157.6 |
| 5,374,629 | 12/1994 | Calverley et al. | 514/167 |
| 5,449,668 | 9/1995 | Sestelo et al. | 514/167 |
| 5,518,725 | 5/1996 | Daynes et al. | 424/212.1 |

(List continued on next page.)

FOREIGN PATENT DOCUMENTS

| | | |
|---|---|---|
| 0 503 630 A1 | 9/1992 | (EP) . |
| 0 562 497 A1 | 9/1993 | (EP) . |
| 664287 | 7/1995 | (EP) . |
| WO 92/05130 | 4/1992 | (WO) . |
| WO 92/12165 | 7/1992 | (WO) . |
| WO 93/14763 | 8/1993 | (WO) . |
| WO 9400128 | 1/1994 | (WO) . |
| WO 9405630 | 3/1994 | (WO) . |
| WO 94/16711 | 8/1994 | (WO) . |
| WO 9640154 | 12/1996 | (WO) . |

OTHER PUBLICATIONS

Engstrom, G. W. and N. J. Koszewski, "Metabolism of Vitamin D2 in Pig Liver Homogenates: Evidence for a Free Radical Reaction", Archives of Biochemistry and Biophysics, vol. 270, No. 2, May 1, pp. 432–440, 1989.

M. F. Holick et al., Proc. Natl. Acad. Sci. USA 68, 803–804 (1971).

G. Jones et al., Biochemistry 14, 1250–1256 (1975).

M. F. Holick et al., Science 180, 190, 191 (1973).

H. Y. Lam et al., Science 486, 1038–1040 (1974).

S. M. Ott, C. H. Chesnut, Annals of Int. Med. 1989, 110:267–274.

J. C. Gallagher et al., Annals of Int. Med. 1990, 113:649–655.

J. Aloia et al., Amer. J. Med. 84:401–08 (1988).

M. Shiraki et al., Endocrinol. Japan 32, 305–315 (1985).

G. F. Jensen et al., Clin. Endocrinol . 16, 515–524 (1982).

C. Christiansen et al., Eur. J. Clin. Invest. 11, 305–309 (1981).

O. H. Sorensen et al., Clin. Endocrinol. 7, 169S–175S (1977).

H. Orimo et al., Bone and Mineral 3, 47–52 (1987).

G. Sjoden et al., J. Nutr. 114, 2043–2046 (1984).

G. Sjoden et al., Proc. Soc. Exp. Biol. Med. 178, 432–436 (1985).

The Merck Index, 11th ed. (1989) p. 9932.

J. Bone Min. Res.; 1994; 9;607–614.

Biochem. J., vol. 310, No. 1 (Aug. 15, 1995) pp. 233–241.

Endocrinology, vol. 136, No. 11 (Nov. 1995) pp. 4749–4753.

Miller et al., 52 Cancer Res. (1992) 515–520.

Skowronski et al., 136 Endocrinology 20–26 (1995).

Horst, R. L., Koszewski, N. J. and Reinhardt, T. A., Biochem., 29:578–82 (1990).

White et al., J. Chem. Soc. Perkin Trans. (1993) 759.

Nishigaichi et al., Chem. Lett. (1996) 961.

Manchand et al., 60 J. Org. Chem. (1995) 6574.

Strugnell et al., Biochem J., 310: 233–241 (1995).

Primary Examiner—Theodore J. Criares
(74) Attorney, Agent, or Firm—Michael Best & Friedrich LLP; Teresa J. Welch

(57) ABSTRACT

The invention provides 24-hydroxyvitamin D compounds and methods for their use in the treatment and prophylaxis of hyperparathyroidism and hyperproliferative diseases, and in the modulation of the immune and inflammatory responses as well as the treatment of bone depletive disorders.

14 Claims, 4 Drawing Sheets

U.S. PATENT DOCUMENTS

| | | | |
|---|---|---|---|
| 5,540,919 | 7/1996 | Daynes et al. | 424/85.2 |
| 5,559,107 | 9/1996 | Gates et al. | 514/167 |
| 5,561,123 | 10/1996 | DeLuca et al. | 514/167 |
| 5,562,910 | 10/1996 | Daynes et al. | 424/278 |
| 5,585,368 | 12/1996 | Steinmeyer et al. | 514/167 |
| 5,589,471 | 12/1996 | Hansen et al. | 514/167 |
| 5,665,387 | 9/1997 | Mathieu et al. | 424/464 |
| 5,700,791 | 12/1997 | Steinmeyer et al. | 514/167 |
| 5,710,142 | 1/1998 | Calverley et al. | 514/167 |
| 5,710,294 | 1/1998 | DeLuca et al. | 552/653 |
| 5,716,946 | 2/1998 | DeLuca et al. | 514/167 |
| 5,750,517 | 5/1998 | Baggiolini et al. | 514/167 |
| 5,750,746 | 5/1998 | DeLuca et al. | 552/653 |
| 5,972,917 | 10/1999 | Bishop et al. | 514/167 |

\* cited by examiner

24-HYDROXYVITAMIN D, ANALOGS AND USES THEREOF

CROSS-REFERENCE TO RELATED APPLICATIONS

This application is a continuation-in-part of U.S. patent application Ser. No. 08/907,659, filed Aug. 8, 1997, now U.S. Pat. No. 5,869,473.

BACKGROUND OF THE INVENTION

This invention relates generally to 24-hydroxyvitamin D compounds and their use in the treatment and prophylaxis of hyperparathyroidism and hyperproliferative diseases, and in the modulation of the immune response as well as the treatment of bone depletive disorders.

Vitamin D has long been established as having an important biological role in bone and mineral metabolism. For example, vitamin D plays a critical role in stimulating calcium absorption and regulating calcium metabolism. The discovery of active forms of vitamin D, (M. F. Holick et al., 68 *Proc. Natl. Acad. Sci. USA*, 803–804 (1971); G. Jones et al., 14 *Biochemistry*, 1250–1256 (1975)), and active vitamin D analogs (M. F. Holick et al., 180 *Science* 190–191 (1973); H. Y. Lam et al., 186 *Science* 1038–1040 (1974)) caused much excitement and speculation about the usefulness of these vitamin D compounds in the treatment of bone depletive disorders.

Animal studies examining the effects of these active vitamin D compounds suggested that such agents would be useful in restoring calcium balance. An early clinical study indicated that administration of 0.5 μg/day of 1α,25-dihydroxyvitamin $D_3$, the hormonally active form of vitamin $D_3$, to a group of postmenopausal women improved intestinal calcium absorption as well as calcium balance in the women. On this basis, U.S. Pat. No. 4,225,596 ("'596 Patent") described and claimed the use of 1α,25-dihydroxyvitamin $D_3$ and analogs thereof for increasing calcium absorption and retention.

The best indicator of the efficacy of vitamin D compounds in the prevention or treatment of depletive bone disorders, however, is bone itself rather than calcium absorption or calcium balance. More recent clinical data indicate that, at the dosage ranges taught in the '596 Patent, 1α,25-dihydroxyvitamin $D_3$ has, at best, modest efficacy in preventing or restoring loss of bone mass or bone mineral content (S. M. Ott and C. H. Chesnut, 110 *Ann. Int. Med.* 267–274 (1989); J. C. Gallagher et al., 113 *Ann. Int. Med.* 649–655 (1990); J. Aloia et al., 84 *Amer. J. Med.* 401–408 (1988)).

These clinical studies with 1α,25-dihydroxyvitamin $D_3$, and another conducted with 1α-hydroxyvitamin $D_3$ (M. Shiraki et al., 32 *Endocrinol. Japan* 305–315 (1985)), indicate that the capacity of these two vitamin D compounds to restore lost bone mass or bone mineral content is dose-related. The studies also indicate, however, that, at the dosage ranges required for either compound to be truly effective, toxicity in the form of hypercalcemia and hypercalciuria becomes a major problem. Specifically, attempts to increase the amount of 1α,25-dihydroxyvitamin $D_3$ above 0.5 μg/day have frequently resulted in toxicity. At dosage levels below 0.5 μg/day, no effects are observed on bone mass or mineral content. (See, G. F. Jensen et al., 16 *Clin. Endocrinol.* 515–524 (1982); C. Christiansen et al., 11 *Eur. J. Clin. Invest.* 305–309 (1981)).

Data from clinical studies in Japan, a population that has low calcium intake, indicate that efficacy is found with 1α-hydroxyvitamin $D_3$ when administered at 1 μg/day (M. Shiraki et al., 32 *EndocrinoL Japan.* 305–315 (1985); H. Orimo et al., 3 *Bone and Mineral* 47–52 (1987)). Two μg/day of 1α-hydroxyvitamin $D_3$ was found to have efficacy in increasing bone mass in patients exhibiting senile osteoporosis (O. H. Sorensen et al., 7 *Clin. Endocrinol.* 169S–175S (1977)). At 2 μg/day, however, toxicity with 1α-hydroxyvitamin $D_3$ occurs in approximately 67 percent of the patients, and at 1 μg/day, this percentage is approximately 20 percent. Thus, these 1α-hydroxylated vitamin $D_3$ compounds can produce dangerously elevated blood calcium levels due to their inherent calcemic activity.

Because of this toxicity, 1-hydroxylated vitamin $D_3$ compounds can only be administered at dosages that are, at best, modestly beneficial in preventing or treating loss of bone or bone mineral content. Indeed, Aloia recommends that alternative routes of administration be sought which might avoid the toxicity problems and allow higher dosage levels to be achieved. (J. Aloia et al., 84 *Amer. J. Med.* 401–408 (1988).) Yet, despite reported toxicities of 1α-hydroxyvitamin $D_3$ and 1α,25-dihydroxyvitamin $D_3$, these two compounds remain the drugs of choice for many bone depletive disease treatments.

These two drugs also remain the only approved forms of 1α-hydroxylated vitamin D for treating or preventing hyperparathyroidism which occurs secondary to end stage renal disease, although both drugs are not currently approved in all major pharmaceutical markets. Hyperparathyroidism is a generalized disorder resulting from excessive secretion of parathyroid hormone (PTH) by one or more parathyroid glands. It is thus characterized by elevated blood levels of parathyroid hormone. Typically, one or more parathyroid glands reveal a marked enlargement. In the case of primary hyperparathyroidism, the glandular enlargement is usually due to a neoplasm or tumor. In the case of secondary hyperparathyroidism, the parathyroid gland hyperplasia typically occurs because of resistance to the metabolic actions of the hormone. Secondary hyperparathyroidism occurs in patients with, e.g., renal failure, osteomalacia, and intestinal malabsorption syndrome. In both primary and secondary hyperparathyroidism, bone abnormalities, e.g., the loss of bone mass or decreased mineral content, are common and renal damage is possible. Hyperparathyroidism is thus also characterized by abnormal calcium, phosphorus and bone metabolism.

More recently, other roles for vitamin D have come to light. Specific nuclear receptors for 1α,25-dihydroxyvitamin $D_3$ have been found in cells from diverse organs not involved in calcium homeostasis. For example, Miller et al., 52 *Cancer Res.* (1992) 515–520, have demonstrated biologically active, specific receptors for 1α,25-dihydroxyvitamin $D_3$ in the human prostatic carcinoma cell line, LNCaP.

It has been reported that certain vitamin D compounds and analogs are potent inhibitors of malignant cell proliferation and inducers/stimulators of cell differentiation. For example, U.S. Pat. No. 4,391,802 issued to Suda et al. discloses that 1α-hydroxyvitamin D compounds, specifically, 1α,25-dihydroxyvitamin $D_3$ and 1α-hydroxyvitamin $D_3$, possess potent antileukemic activity by virtue of inducing the differentiation of malignant cells (specifically, leukemia cells) to nonmalignant macrophages (monocytes), and are useful in the treatment of leukemia. In another example, Skowronski et al., 136 *Endocrinology* 20–26 (1995), have reported antiproliferative and differentiating actions of 1α,25-dihydroxyvitamin $D_3$ and other vitamin $D_3$ analogs on prostate cancer cell lines.

Previous proliferation studies, such as those cited above, focused exclusively on vitamin $D_3$ compounds. Even though such compounds may, indeed, be highly effective in differentiating malignant cells in culture, their practical use in differentiation therapy as anticancer agents is severely limited because of their equally high potency as agents affecting calcium metabolism. At the levels required in vivo for effective use as antileukemic agents, these same compounds can induce markedly elevated and potentially dangerous blood calcium levels by virtue of their inherent calcemic activity. In other words, the clinical use of 1α,25-dihydroxyvitamin $D_3$ and other vitamin $D_3$ analogs as anticancer agents is precluded, or severely limited, by the risk of hypercalcemia.

Still other metabolic conditions in which it has been suggested that vitamin D plays a role are immune response (see, e.g., U.S. Pat. No. 4,749,710 issued to Truitt et al.; U.S. Pat. No. 5,559,107 issued to Gates et al.; U.S. Pat. Nos. 5,540,919, 5,518,725 and 5,562,910 issued to Daynes et al.) and inflammatory response (e.g., U.S. Pat. No. 5,589,471 issued to Hansen et al.).

Considering the diverse biological actions of vitamin D and its potential as a therapeutic agent, a need exists for compounds with greater specific activity and selectivity of action, e.g., vitamin D compounds with antiproliferative and differentiating effects but which have less calcemic activity than therapeutic amounts of the known compounds or analogs of vitamin $D_3$.

BRIEF SUMMARY OF THE INVENTION

The present invention provides 24-hydroxyvitamin D compounds represented by general formula (I) described hereinafter, wherein the C-17 sidechain is a saturated or unsaturated, substituted or unsubstituted, straight or branched $C_4$–$C_{18}$ hydrocarbon group in which the C-24 or equivalent position is hydroxylated. The invention also provides a method for treating or preventing certain diseases and disorders. Such diseases and disorders include (i) hyperparathyroidism by lowering (or maintaining low) serum parathyroid hormone levels; (ii) hyperproliferative diseases; (iii) immune response imbalance; (iv) inflammatory diseases; and (v) bone depletive disorders.

The compound of formula (I) is a 24-hydroxyvitamin D compound which has potent biological activity but low calcemic activity relative to the active forms of vitamin $D_3$. Preferably such compounds are 24-hydroxylated prodrugs which are hydroxylated in vivo at the C-1 position to form 1,24-dihydroxylated active vitamin D compounds.

As used herein, the term "vitamin D compound" is meant to refer to compounds which fall within the generic structure of formula (I) and such compound or its metabolite exhibits vitamin D hormonal bioactivity. It is also noted that a shorthand notation is often used for the D compounds, e.g., 1α-hydroxyvitamin $D_2$ may be referred to as simply 1α-OH-$D_2$.

In another aspect, the invention is a pharmaceutical composition in which the compound of formula (I) is the active ingredient. Such composition is suitably presented in unit dosage form having an effective amount of a vitamin D compound of formula (I) and a pharmaceutically acceptable excipient.

The treatment methods of the present invention are alternatives to conventional therapies with 1α,25-dihydroxyvitamin $D_3$ or 1α-hydroxyvitamin $D_3$. The methods are characterized as providing the compound of formula (I) having equivalent bioactivity but much lower toxicity than these conventional therapies.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWING(S)

The preferred exemplary embodiment of the present invention will hereinafter be described in conjunction with the appended drawing wherein like designations refer to like elements throughout and in which.

DETAILED DESCRIPTION OF THE INVENTION

Figure 1:
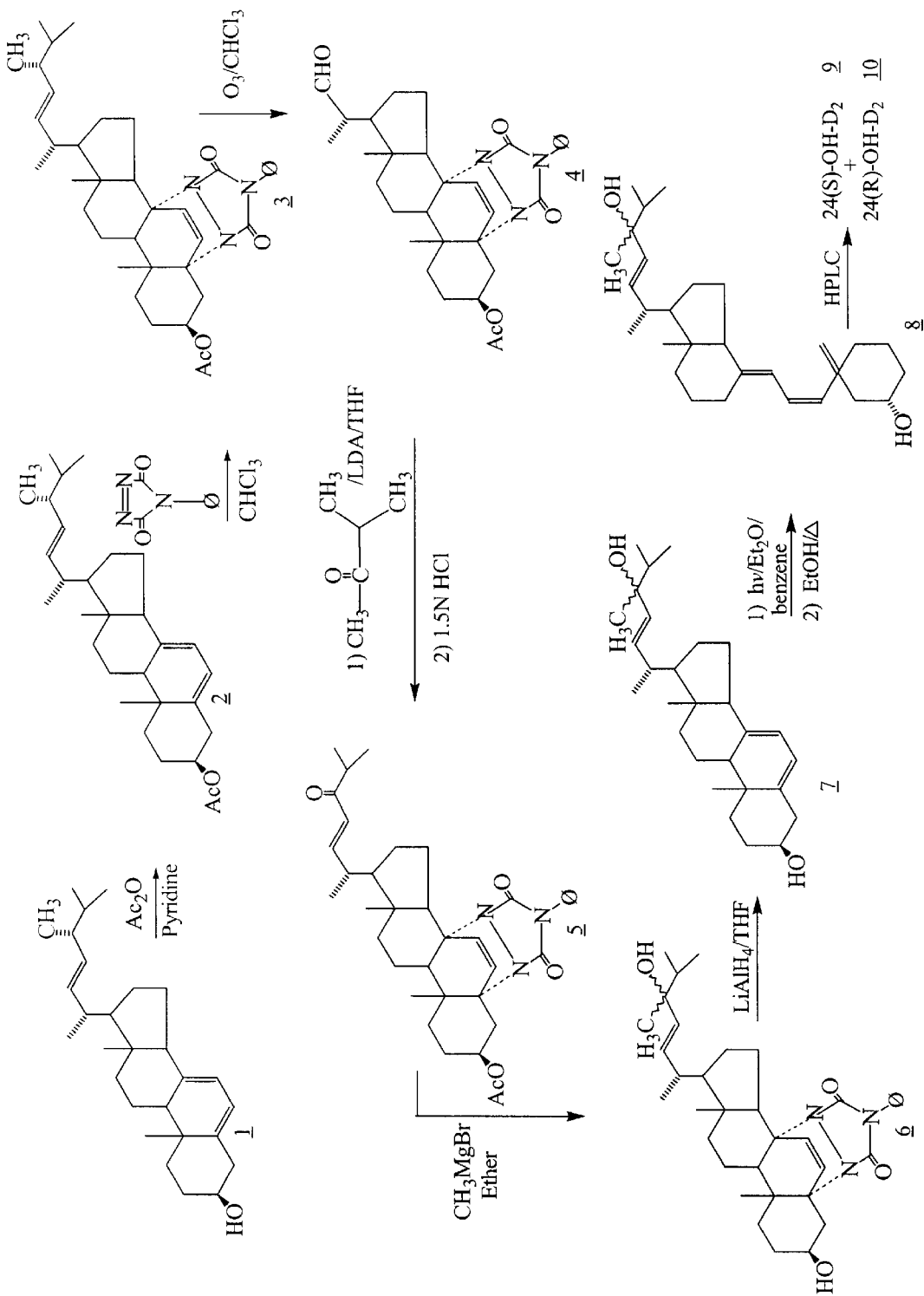
FIG. 1 is an exemplary reaction scheme for the preparation of 24-hydroxyvitamin $D_2$.

The present invention relates 24-hydroxyvitamin D compounds. The compounds of the present invention are most particularly adapted for use in the treatment and prophylaxis of certain diseases and disorders, e.g., hyperproliferative and inflammatory diseases, hyperparathyroidism, bone depletive disorders and certain immune response conditions. Such hyperproliferative diseases include skin, breast, colon and prostate cancer and psoriasis. Inflammatory diseases include arthritis and asthma. Hyperparathyroid diseases include both primary and secondary hyperparathyroidism. Immune response conditions include autoimmune diabetes, multiple sclerosis and transplant rejection. Accordingly, the present invention will now be described in detail with respect to such endeavors; however, those skilled in the art will appreciate that such a description of the invention is meant to be exemplary only and should not be viewed as limitative on the full scope thereof.

The present invention provides 24-hydroxyvitamin D compounds which find value as pharmaceutical agents. These compounds are suitably prodrugs for 1α,24-dihydroxylated vitamin D compound as they are hydroxylated in vivo at the 1α-position to become active forms of vitamin D. As prodrugs, these compounds, in effect, by-pass the first-pass concern over intestinal vitamin D receptor binding which mediates intestinal calcium absorption, thereby resulting in reduced or no hypercalcemia compared with similar dosing with known active vitamin D compounds such as 1α,25-dihydroxyvitamin $D_3$ and 1α-hydroxyvitamin $D_3$.

In the following description of the method of the invention, process steps are carried out at room temperature and atmospheric pressure unless otherwise specified.

As used herein, the terms "substantially pure" or "substantially free" refer to a purity of at least 90%. The term "substantially less" refers to at least 25% less than the comparative substance. Also, as used herein, the term "lower" as a modifier for alkyl, alkenyl, fluoroalkyl, fluoroalkenyl or cycloalkyl is meant to refer to a straight or branched, saturated or unsaturated hydrocarbon group having 1 to 4 carbon atoms. Specific examples of such hydrocarbon groups are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. As used herein, the term "hydrocarbon moiety" refers to a lower alkyl, a lower alkenyl, a lower acyl group or a lower cycloalkyl, i.e., a straight or branched, saturated or unsaturated $C_1$–$C_4$ hydrocarbon group. Also, the term "equivalent position," as in, e.g., C-24 or equivalent position, is meant to refer to a particular carbon in the C-17 side chain of a vitamin D compound wherein that carbon would be the C-24 carbon but for homologation of the side chain.

In one aspect, vitamin D compounds operable in the present invention are suitably represented by formula (I):

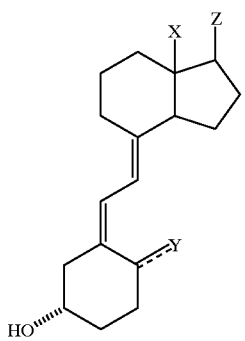

(I)

wherein Z represents a saturated or unsaturated, substitued or unsubstituted, straight-chain or branched $C_4$–$C_{18}$ hydrocarbon group in which the C-24 or equivalent position is hydroxylated; Y is a methylene group if Y is double bonded to the A-ring or a methyl or hydrogen if Y is single bonded, i.e., when Y is hydrogen, the compound of formula (I) is a 19-nor compound; and X is hydrogen, lower alkyl or lower fluoroalkyl. It is noted that when X is hydrogen, the compound of formula (I) is an 18-nor compound.

Preferably, Z is a side chain represented by formula (IIA):

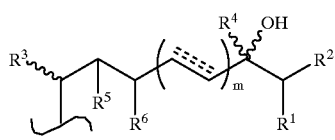

(IIA)

wherein m is 0 or 1 and a dotted line along the side chain represents an optional additional C—C bond; $R^1$ and $R^2$ are independently lower alkyl, lower fluoroalkyl, lower alkenyl, lower fluoroalkenyl, lower cycloalkyl or, taken together with the carbon to which they are bonded (e.g., C-25 in the case where m=0), form a $C_3$–$C_8$ cyclohydrocarbon ring; $R^3$ is hydrogen, lower alkyl, lower fluoroalkyl, lower alkenyl or lower fluoroalkenyl; $R^4$ is lower alkyl, lower fluoroalkyl, lower alkenyl or lower fluoroalkenyl; $R^5$ and $R^6$ are each hydrogen or taken together form a double bond between C-22 and C-23. As to the bond to which m refers, this bond may be a single, double or triple bond, in other words, a —$CH_2$—$CH_2$—, a —CH=CH— or a —C≡C—.

For example, Z includes a side chain represented by formula (IIB):

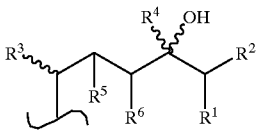

(IIB)

wherein $R^5$ and $R^6$ are each hydrogen or taken together form a double bond between C-22 and C-23, $R^3$ is hydrogen, lower alkyl, lower fluoroalkyl, lower alkenyl or lower fluoroalkenyl; $R^4$ is lower alkyl, lower fluoroalkyl, lower alkenyl or lower fluoroalkenyl; and $R^1$ and $R^2$ are independently hydrogen, lower alkyl, lower fluoroalkyl, lower alkenyl, lower fluoroalkenyl, lower cycloalkyl or taken together with the carbon to which they are bonded (i.e., C-25) form a $C_3$–$C_8$ cyclocarbon ring.

Z also includes a side chain represented by formula (IIC):

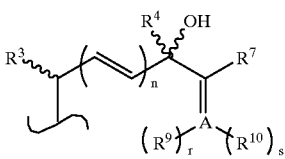

(IIC)

wherein n is an integer which is 1 or 2; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and S is zero when A is nitrogen; r and s are 1 when A is carbon; r and s are zero when A is sulfur or oxygen; and $R^9$ and $R^{10}$ are independently hydrogen, lower alkyl, lower alkenyl, lower fluoroalkyl or lower fluoroalkenyl. As to the bond to which m refers, this bond is a —$CH_2$—$CH_2$— or a —CH=CH—.

For example, Z includes a side chain wherein n is 1, A is carbon and r and s are 1 and which is represented by formula (IID):

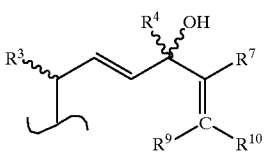

(IID)

wherein $R^3$, $R^9$ and $R^{10}$ are independently hydrogen, lower alkyl, lower fluoroalkyl, lower alkenyl or lower fluoroalkenyl, and $R^4$ and $R^7$ are independently lower alkyl, lower fluoroalkyl, lower alkenyl or lower fluoroalkenyl.

Also, Z includes a side chain represented by formula (IIE):

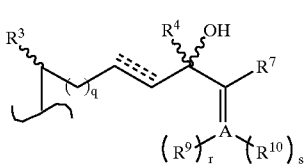

(IIE)

wherein a dotted line along the side chain represents an optional additional C—C bond; q is zero or an integer which is 1 or 2; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^9$ and $R^{10}$ are independently hydrogen, lower alkyl, lower alkenyl, lower fluoroalkyl or lower fluoroalkenyl. As to the optional additional bonds, for example, when q=0, there may be a single, double or triple bond between C-22 and C-23. As to the group to which q refers, this group is —$CH_2$—.

For example, Z includes a side chain wherein q is zero, A is carbon, r and s are 1; $R^3$, $R^9$ and $R^{10}$ are hydogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; and which is represented by formula (IIF):

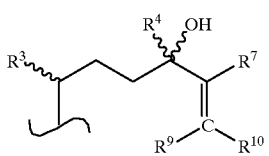

(IIF)

Also included as vitamin D compounds within the scope of the present invention are 24-hydroxyprevitamin D compounds which suitably include the same Z side chain described above including those represented by formulas (IIA), (IIB), (IIC), (IID), (IIE) and (IIF) that are hydroxysubstituted at C-24 or equivalent position. Previtamin D compounds are the thermal isomers of the corresponding vitamin D compounds, e.g., 24-hydroxyprevitamin $D_2$ is the thermal isomer of 24-hydroxyvitamin $D_2$, and exists in thermal equilibrium with same. 24-Hydroxyprevitamin D compounds in accordance with the present invention are suitably represented by formula (III):

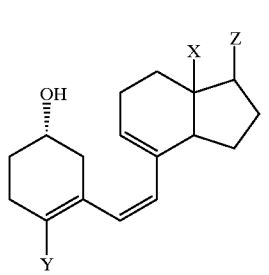

(III)

wherein X, Y and Z are as described above.

Preferred among the compounds of formula (I) are the 24-hydroxy compounds which are prodrugs for 1α,24-dihydroxylated vitamin D. Examples of the compounds of formula (I) are:
24-hydroxyvitamin $D_2$ [24-(OH)-$D_2$];
24-hydroxy-25-fluorovitamin $D_2$ [24-(OH)-25F-$D_2$];
24-hydroxy-25-ene-vitamin $D_2$ [24-OH-25-ene-$D_2$];
24-hydroxy-25-oxo-vitamin $D_2$ [24-OH-25-oxo-$D_2$];
24-hydroxyvitamin $D_4$[24-(OH)-$D_4$];
24-hydroxy-25-fluorovitamin $D_4$ [24-(OH)-25-F-$D_4$];
24-hydroxy-25-ene-vitamin $D_4$ [24-OH-25-ene-$D_4$]; and
24-hydroxy-25-oxo-vitamin $D_4$ [24-OH-25-oxo-$D_4$].
Preferred among the compounds of formula (III) are the 24-hydroxy previtamin D compounds which are prodrugs and isomers for 1α,24-dihydroxylated vitamin D. Examples of the compounds of formula (III) are:

24-hydroxyprevitamin $D_2$ [24-(OH)-pre$D_2$];
24-hydroxy-25-fluoroprevitamin $D_2$ [24-(OH)-25-F-pre$D_2$];
24-hydroxy-25-ene-previtamin $D_2$ [24-OH-25-ene-pre$D_2$];
24-hydroxy-25-oxo-previtamin $D_2$ [24-OH-25-oxo-pre$D_2$];
24-hydroxyprevitamin $D_4$[24-(OH)-pre$D_4$];
24-hydroxy-25-fluoroprevitamin $D_4$ [24-(OH)-25-F-pre$D_4$];
24-hydroxy-25-ene-previtamin $D_4$ [24-OH-25-ene-pre$D_4$]; and
24-hydroxy-25-oxo-previtamin $D_4$ [24-OH-25-oxo-pre$D_4$].

Among those compounds of the present invention that have a chiral center in the sidechain, such as at C-20 or C-24, it is understood that both diastereomers (e.g., R and S) and the mixture thereof are within the scope of the present invention.

The compounds of formula (I) may generally be prepared by the exemplary reaction process depicted in FIG. 1. FIG. 1 illustrates a method of preparing 24-hydroxyvitamin $D_2$ using ergosterol as a starting material and forming 24-hydroxyvitamin $D_2$ which is then separated to yield the 24(S)-hydroxyvitamin $D_2$ diastereomer and the 24(R)-hydroxyvitamin $D_2$ diastereomer, if stereochemical purity is desired. Hereinafter when reference is made to a 24-hydroxy compound, unless otherwise specified, it will be presumed that the compound is a diastereomeric mixture of the R and S forms.

Specifically, ergosterol is converted to 24-hydroxyergosterol (5,7,22 ergostatriene-3β,24-diol (7)) by a six-step process. The 24-hydroxyergosterol is then irradiated and thermally converted by methods well known in the art to yield 24-hydroxyvitamin $D_2$ from which the diastereomers are separated.

As seen in FIG. 1, ergosterol is acetylated to form the 3β-acetate (2). An adduct (3) is then formed with the B-ring of the ergosterol structure by reaction of the 3β-acetate with a triazoline dione. The adduct (3) is then ozonated to truncate the side chain to form a C-21 aldehyde (4). The side chain is reestablished by reaction of the resulting aldehyde with the appropriate keto-compound to yield the 24-enone (5). The enone is then converted to the 24-methyl, 3β,24-dihydroxy adduct (6). This adduct is then reacted with a lithium aluminum hydride to deprotect the adduct and yield 24-hydroxyergosterol (7). The 24-hydroxyergosterol is then irradiated and thermally treated to form 24-hydroxyvitamin $D_2$ (8). The 24-hydroxyvitamin $D_2$ is subjected to reverse phase high pressure liquid chromatography to separate the two diastereomers and recover the diastereomeric forms of the invention, 24(S)-hydroxyvitamin $D_2$ (9) and 24(R)-hydroxyvitamin $D_2$ (10).

Figure 2:
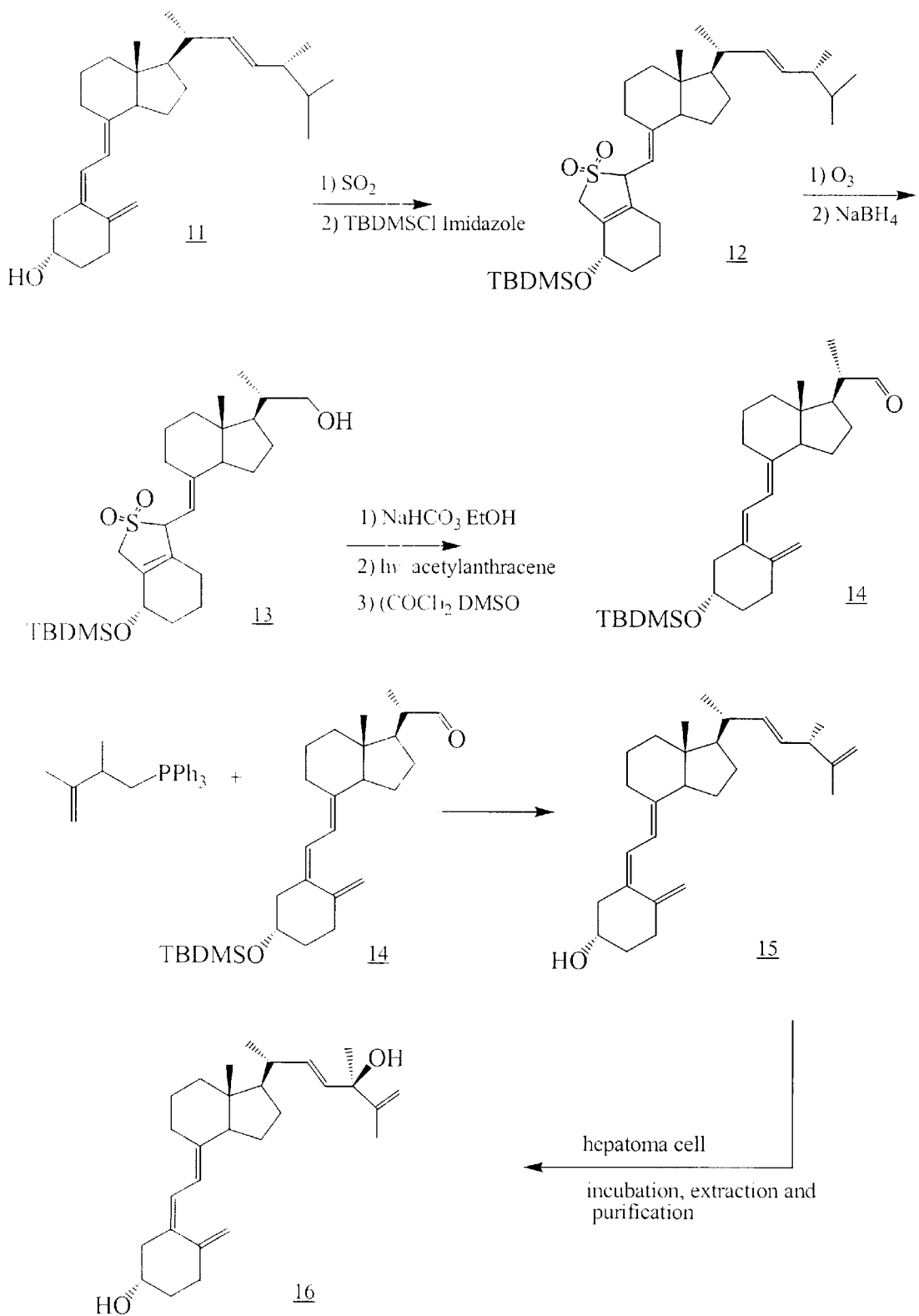
FIG. 2 is an exemplary reaction scheme for the preparation of 24-hydroxy-25-ene-vitamin $D_2$.

The compounds of formula (I) wherein the side chain is represented by formulas (IIC) or (IIE) may generally be prepared by the exemplary reaction process depicted in FIG. 2. FIG. 2 illustrates a method of preparing 24-hydroxy-25-ene-vitamin $D_2$ entails using vitamin $D_2$ as a starting material and forming 25-ene-vitamin $D_2$, incubating cultured cells derived from human hepatoma cells, e.g., HEP3B or HEPG2, with the 25-ene-vitamin $D_2$ to yield the metabolite 24-hydroxy-25-ene-vitamin $D_2$ which is then isolated and purified by high pressure liquid chromatography.

As seen in FIG. 2, vitamin $D_2$ (11) is reacted with $SO_2$ and the hydroxyl functionality at C-3 is protected with t-butyl dimethylsilylchloride affording the intermediate (12). Ozonolysis and reduction affords the alcohol (13). $SO_2$ extrusion, isomerization and subsequent oxidation using the known Swern oxidation affords the aldehyde (14). The side chain is introduced by reaction of aldehyde (14) with Wittig reagent to yield the 25-ene-vitamin $D_2$ compound (15). The 25-ene compound (15) is then incubated with a cell line derived from human hepatoma cells, and the 24-hydroxy-25-ene-vitamin $D_2$ (16) is extracted and purified.

The compounds of formula (III) may be generally prepared by the processes of FIGS. 1 and 2 wherein the previtamin starting materials can be prepared by the exemplary reaction processes given in, e.g., U.S. Pat. No. 5,252,191 issued to Pauli et al.; U.S. Pat. No. 5,035,783 issued to Goethals et al; U.S. Pat. No. 4,388,243, all of which are incorporated herein by reference. The 19-nor compounds of formula (1) may be generally prepared by the exemplary reaction processes given herein wherein the 19-nor starting materials can be prepared by the exemplary processes given in, e.g., U.S. Pat. No. 5,710,294, incorporated herein by reference, using the appropriate vitamin D starting material.

The compounds of the present invention are useful as active compounds in pharmaceutical compositions having reduced side effects and low toxicity as compared with the known analogs of active forms of vitamin $D_3$. The compounds are especially of value for both local, including topical, and systemic treatment and prophylaxis of human and veterinary disorders which are characterized by (i) abnormal cell proliferation and/or cell differentiation, e.g., cancers such as skin, breast, colon and prostate and dermatological disorders such as psoriasis; (ii) imbalance of the immune system, e.g., autoimmune diseases such as multiple sclerosis and diabetes, and rejection of transplants; (iii) abnormal interleukin-1 production, e.g., inflammatory response diseases such as rheumatoid arthritis and asthma; (iv) abnormal parathyroid hormone production, e.g., hyperparathyroidism, both primary and secondary; and (v) loss of bone mass or bone mineral content, e.g., osteoporosis.

The 24-hydroxyvitamin D compounds of the present invention are those that have a lower tendency or inability to cause the undesired side effects of hypercalcemia and/or hypercalciuria. In other words, the compounds of the present invention can be administered at dosages that allow them to act, e.g., as antiproliferative agents and cell differentiation agents when exposed to malignant or other hyperproliferative cells, without significantly altering calcium metabolism. This selectivity and specificity of action makes the 24-hydroxyvitamin D compounds of the present invention useful and preferred agents for, e.g., safely inhibiting hyperproliferation and promoting malignant or hyperplastic cell differentiation. The 24-hydroxyvitamin D compounds of the present invention, thus, overcome the shortcomings of the known active vitamin $D_3$ compounds described above, and can be considered preferred agents for the control and treatment of malignant diseases such as prostate cancer as well as benign prostatic hyperplasia, skin diseases, such as skin cancer and psoriasis, breast cancer and colon cancer, immune and inflammatory response disorders, and hyperparathyroidism as well as bone depletive disorders.

The pharmacologically active compounds of this invention are suitably processed in accordance with conventional methods of pharmacy to produce medicinal compositions for administration to patients, e.g., mammals including humans, in, e.g., admixtures with conventional excipients such as pharmaceutically acceptable organic or inorganic carrier substances which do not deleteriously react with the active compounds, and optionally, other therapeutic ingredients. Any suitable route of administration may be employed for providing an effective dosage of the compounds in accordance with the present invention. For example, oral, rectal, topical, parenteral, intravenous, intramuscular, subcutaneous, ocular, nasal, buccal, and the like routes may be employed.

Therapeutic and prophylactic compositions are those suitable for the various routes of administration described herein, although the most suitable route in any given case will depend on the nature and severity of the condition being treated and on the nature of the active ingredient. The compositions are conveniently presented in unit dosage form.

Suitable pharmaceutically acceptable carriers for use in the composition and method of the present invention include, but are not limited to water, salt solutions (e.g., buffer solutions), alcohols including benzyl alcohols, gum arabic, mineral and vegetable oils (e.g., corn oil, cottonseed oil, peanut oil, olive oil, coconut oil), fish liver oils, oily esters such as Polysorbate 80, polyethylene and propylene glycols, gelatin, carbohydrates (e.g., lactose, amylose or starch), magnesium stearate, talc, silicic acid, viscous paraffin, fatty acid monoglycerides and diglycerides, pentaerythritol fatty acid esters, hydroxymethylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring and flavoring. If a solid carrier is used, the dosage form of the compounds of the present invention may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

It is noted, however, that dosage forms of 24-hydroxyprevitamin D are most suitably formulated with carriers such as starch, lactose or amylose, which do not deleteriously react with the active compounds. The formulations can be produced in tablet, capsule, powder, and lozenge form. However, whatever method of formulation is used, care should be taken to avoid exposure to solvents and heat as, under such conditions, there is a tendency for 24-hydroxyprevitamin D to convert to 24-hydroxyvitamin D, i.e., the compounds of formula (III) are preferably formulated in solvent-free, crystalline, heat-stable form. Because heat and solvents are to be avoided, the preferred method of tablet formulation is dry granulation.

For parenteral application, particularly suitable are injectable, sterile solutions, preferably oily or aqueous solutions, as well as suspensions, emulsions, or implants, including suppositories. Ampules are convenient unit dosages. The dosage of the analogs in accordance with the present invention for parenteral administration generally is about 1–30 $\mu$g given 1 to 3 times per week.

As noted above, for enteral application, particularly suitable are tablets, dragées, liquids, drops, suppositories, or capsules. A syrup, elixir, or the like can also be used wherein a sweetened vehicle is employed.

For rectal administration, compounds are formed into a pharmaceutical composition containing a suppository base such as cacao oil or other triglycerides. To prolong storage life, the composition advantageously includes an antioxidant, such as ascorbic acid, butylated hydroxyanisole or hydroquinone.

For topical application, there are also employed as non-sprayable forms, viscous to semi-solid or solid forms comprising a carrier compatible with topical application and having a dynamic viscosity preferably greater than water. Suitable topical formulations include transdermal devices, solutions, suspensions, emulsions, aerosols, creams, ointments, liniments, salves, lotions, dusting powders and the like which are, if desired, sterilized or mixed with auxiliary agents, e.g., preservatives, etc.

The magnitude of a prophylactic or therapeutic dose of the compounds in accordance with the present invention will vary with the nature or the severity of the condition to be treated and with the particular composition and its route of administration. Oral administration of the pharmaceutical compositions of the present invention is preferred.

In general, the daily dosage of the compounds according to this invention is about 0.025 to about 7.5 nmol/kg of body weight of the patient, preferably about 0.025 to about 1 nmol/kg. The compounds of this invention are suitably dispensed by unit dosage form in a pharmaceutically acceptable carrier, e.g., a unit dosage form including about 0.25 to about 50.0 µg in a pharmaceutically acceptable carrier per unit dosage. The dosage of the compounds according to the present invention generally is about 3.5 µg to about 1000 µg/week, preferably about 10 µg to about 500 µg/week.

For treatment of hyperproliferative diseases such as cancers and psoriasis, the enteral dosage of the compounds of the present invention is about 1 nmol to about 100 nmol per unit dosage; for hyperparathyroidism, about 0.5 nmol to 50 nmol per unit dosage; for treatment of inflammatory diseases, about 1 nmol to 150 nmol per unit dosage; for immune response modulation, about 1 nmol to 150 nmol per unit dosage; and for bone depletive diseases, about 1 nmol to 150 nmol per unit dosage. In terms of micrograms, the effective dosage amount on a daily basis per kilogram of body weight of the patient ranges from about 0.01 µg/kg/day to about 3.0 µg/kg/day.

In addition, those skilled in the art will also appreciate that such dosages may be encapsulated in time release, e.g., sustained, delayed or directed release, delivery systems such as a liposome delivery system, polysaccharides exhibiting a slow release mechanism, salistic or other polymer implants or microspheres, as well as those where the active ingredient is suitably protected with one or more differentially degradable coatings, e.g., by microencapsulation, enteric coating, multiple coatings, etc., and such means effect continual dosing of compositions contained therein. For example, an enteric coating is suitably one which is resistant to disintegration in gastric juice. It is also possible to freeze-dry the active ingredient and use the lyophilizate obtained, e.g., for the preparation of products for injection.

It will be appreciated that the actual preferred amounts of active analog in a specific case will vary according to the specific compound being utilized, the particular compositions formulated, the mode of application, and the particular sites being treated. Dosages can be determined using conventional considerations, e.g., by customary comparison of the differential activities of the subject compounds and of a known agent, e.g., by means of an appropriate conventional pharmacological protocol.

The specific doses for each particular patient depend on a wide variety of factors, for example, on the efficacy of the specific compound employed, on the age, body weight, general state of health, sex, on the diet, on the timing and mode of administration, on the rate of excretion, and on medicaments used in combination and the severity of the particular disorder to which the therapy is applied.

As described hereinbefore, the compounds of the present invention are preferably administered to the human (or veterinary) patients in oral dosage formulation. As a compound in accordance with the present invention is released from the oral dosage formulation, it is absorbed from the intestine into the blood. The compounds of the present invention then undergo hydroxylation at the 1α-position of the A-ring of the vitamin D ring structure, thus providing an active form of the vitamin D compound which is 1α,24-dihydroxylated. As to the compounds of formula (I), little or no first-pass interaction with the intestinal vitamin D receptors is to be expected, thus, yielding little or no stimulation of intestinal calcium absorption. In the case of the 24-hydroxyprevitamin D compounds of formula (III), as these compounds are warmed by the core temperature of the animal or human, they convert to the corresponding 24-hydroxyvitamin D which are then 1α-hydroxylated to form the 1,24-dihydroxy compounds. It is also noted that 24-hydroxyprevitamin D compounds do not interact with the intestinal vitamin D receptors and, thus, do not stimulate first-pass intestinal calcium absorption.

The dosage forms of the compositions of the present invention may also contain adjuvants as well as other therapeutically valuable substances or may contain more than one of the compounds specified herein in admixture. Thus, a further aspect within the scope of the present invention is administration of effective dosages of the compounds of the present invention in conjunction with administration of other hormones or other agents which have been shown to have efficacy in the treatment and prevention of the diseases and disorders described herein. It is anticipated that such co-administration or combination can provide a significantly enhanced therapeutic effect, e.g., a synergistic effect.

For example, as to treatment of bone depletive diseases, compounds of the present invention are suitably co-administered with agents known to ameliorate bone diseases or disorders. Such bone agents include conjugated estrogens or their equivalents, antiestrogens, calcitonin, bisphosphonates, calcium supplements, calcium receptor agonists, cobalamin, pertussis toxin, boron, dehydroepiandrosterone (DHEA) and other bone growth factors such as transforming growth factor beta, activin or bone morphogenic protein. Possible dose ranges for certain of these co-administered agents are provided in Table 1.

TABLE 1

Possible Oral Dose Ranges for Various Agents
Co-Administered With 1α-Hydroxyvitamin $D_3$

| | Dose Ranges | | |
|---|---|---|---|
| Agent | Broad | Preferred | Most Preferred |
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Bisphosphonates (µg/day) | 50–20,000 | 100–15,000 | 250–10,000 |
| Calcium Supplements (mg/day) | 250–2500 | 500–1500 | 750–1000 |
| Calcium Receptor Agonists (mg/day) | 4–1000 | 20–800 | 50–60 |
| Cobalamin (µg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Antiestrogens, such as Tamoxifen™, are also known bone agents as well as antiproliferative agents and may be suitably used in conjunction with the 24-hydroxyvitamin D and 24-hydroxyprevitamin D compounds of the present invention.

Although the above examples detail dosage by mouth, it is to be understood that the combinations of agents can also be administered in alternative fashions, including intranasally, transdermally, intrarectally, intravaginally, subcutaneously, intravenously, and intramuscularly.

Also provided in the present invention is the co-administration of the compounds of the present invention with known cytotoxic agents. Such agents include estramustine phosphate, prednimustine, cisplatin, 5-fluoro-uracil, melphalan, hydroxyurea, mitomycin, idarubicin, methotrexate, adriamycin and daunomycin. It is anticipated that a vitamin D of formula (I) or (III) used in combination with various anticancer drugs can give rise to a significantly enhanced cytotoxic effect on cancerous cells, thus providing an increased therapeutic effect. Specifically, as a significantly increased growth-inhibitory effect is obtained with the above-disclosed combinations utilizing lower concentrations of the anticancer drugs compared to the treatment regimes in which the drugs are used alone, there is the potential to provide therapy wherein adverse side effects associated with the anticancer drugs are considerably reduced compared to those normally observed with the anticancer drugs used alone in larger doses. Possible dose ranges of these co-administered second anticancer agents are about 0.1 to 1 µg/kg/day.

The compounds in accordance with the present invention are also suitably co-administered with known antiinflammatory agents. Such agents include both steroidal (e.g., corticosteroids) and nonsteriodal antiinflammatory agents (e.g., salicylates, naproxen). It is anticipated that a compound of the present invention used in combination with these various antiinflammatory drugs can give rise to a significantly enhanced antiinflammatory activity, thus providing an increased therapeutic effect and an anticipated lower effective dosage of antiinflammatory agents.

Also included with the scope of the present invention is the co-administration of compounds in accordance with the present invention with known immune response augmenting agents. Such agents include the cyclosporins, DHEA and DHEA derivatives such as DHEA-sulfate, 16α-bromo-DHEA, 7-oxo-DHEA, 16α-bromo-DHEA-sulfate and 7-oxo-DHEA-sulfate. It is also anticipated that a compound of the present invention used in combination with these various immune response modulating drugs can give rise to a significantly enhanced immunomodulating activity, thus providing an increased therapeutic effect.

The present invention is further explained by the following examples which should not be construed by way of limiting the scope of the present invention.

EXAMPLE 1

Synthesis of 24-hydroxyvitamin $D_2$[24-OH-$D_2$] (22E)-5,7,22-ergostatriene-3β-yl acetate (2)

To a solution of 50 gm (0.13 mol) of ergosterol (1) in 300 ml of anhydrous pyridine was added 33.3 ml (0.35 mol) of acetic anhydride. The mixture was stirred at room temperature overnight and then 600 ml of water was added. The precipitate was filtered and washed three times with 200 ml portions of acetonitrile and then air dried to yield 42.0 g (74%) of (2).

22-oxo-5α,8α-(4-phenyl-3.5-dioxo- 1,2,4-triazolidine-1.2-diyl) 23,24-dinor-6-cholene-3β-yl acetate (4)

To a solution of 33.0 g (0.075 mol) of ergosterol acetate (2) in 1000 ml of chloroform was added 13.2 g (0.075 mol) of 4-phenyl-1,2,4-triazoline-3,5-dione. The solution of the thus formed (3) was stirred at room temperature for 30 min. and then 5 ml of pyridine was added. The solution was cooled to −78° C. and treated at −78° C. with an ozone-oxygen mixture for 2 hours and then thoroughly purged with nitrogen. Then 50 ml of dimethylsulfoxide was added and the mixture was washed with 300 ml of water, then twice with 200 ml of 2N HCl and finally 300 ml of water. The organic layer was separated, dried over anhydrous $MgSO_4$ and concentrated to dryness in vacuo. The residue was purified on a silica gel column using 30% ethyl acetate in hexane to yield 16.0 g (39%) of the title compound as a foamy solid.

$^1$H NMR: (400 MHZ; $CDCl_3$): δppm 0.85 (3H, s, 18-$CH_3$), 1.10 (3H, s, 19-$CH_3$), 1.15 (3H, d, 21-$CH_3$), 1.99 (3H, s, 3β-$CH_3CO$), 5.45 (1H, m, 3α-H), 6.26 (1H, d. 7-H), 6.40 (1H, d, 6-H), 7.42 (5H, m, Ph), 9.58 (1H, d, HCO).

(22E)5α,8α-(4-phenyl-3,5-dioxo-1,2,4-triazolidine-1,2-diyl) cholesta-6,22-diene-24-one-3β-yl acetate (5)

Butyllithium (1.6M solution in hexane 8.94 ml, 0.014 mol) was added to a stirred, cooled (0° C.) solution of diisopropylamine (1.45 g, 0.014 mol) in dry tetrahydrofuran (20 ml) under nitrogen. 3-Methylbutan-2-one (1.23 g, 0.014 mol) in dry tetrahydrofuran (6 ml) was added dropwise at 0° C. over 15 min. The solution was stirred at 0° C. for 1 hr. more, then cooled to −70° C. and a solution of the aldehyde (4) (6.0 g, 0.011 mol) in dry tetrahydrofuran (60 ml) was added. The temperature was raised to −20° C. and kept at this temperature for 3 hrs. Then glacial acetic acid (20 ml) was added at −20° C. and the solution was brought to room temperature. Ether (800 ml) and water (400 ml) were added and the organic layer was separated and washed with 10% hydrochloric acid (2×300 ml), saturated sodium bicarbonate solution (2×300 ml), and water (2×300 ml). Concentration gave the crude product (7.5 g) which was dissolved in tetrahydrofuran (100 ml) containing 1.5 N-hydrochloric acid (12 ml). After refluxing for 1.5 hrs., the mixture was diluted with ether (600 ml), washed with a 5% sodium carbonate solution (2×200 ml) and water (2×200 ml), and dried (anhydrous $MgSO_4$). Concentration under reduced pressure gave the crude product (7.0 g). Chromatography over silica gel (50% ethyl acetate in hexane) gave the enone (5) 4.0 g (59%).

$^1$H NMR: (400 MHZ): δppm 0.83 (3H, s. 18-$CH_3$), 0.99 (3H, s, 19-$CH_3$), 1.09 (6H, dd, 26 and 27-$CH_3$), 1.12 (3H, d, 21-$CH_3$), 2.0 (3H, s, 3β-$CH_3CO$), 2.84 (1H, m, 25-H), 5.45 (1H, m, 3α-H), 6.06 (1H, d, 23-H), 6.24 (1H, d, 7-H), 6.39 (1H, d, 6-H), 6.71 (1H, dd, 22-H), 7.42 (5H, m, Ph).

(22E)-5α,8α-(4-phenyl-3,5-dioxo-1,2,4-triazolidine-1,2-diyl)-6,22-ergostadiene-3β,24-diol (6)

The enone (5) (3.5 g, 5.7 mmol) in dry ether (100 ml) was cooled to 0° C. and methylmagnesium bromide (3.0 M solution in ether 6.8 ml, 0.02 mol) was added dropwise. After 1 hr. at 0° C., saturated ammonium chloride (100 ml) was added. The organic layer was separated. The aqueous layer was extracted with ether (2×200 ml). The combined ether phases were dried over anhydrous $MgSO_4$ and concentrated to dryness in vacuo to yield the crude product 3.0 g (90%) of (6).

(22E)-5,7,22-ergostatriene-3β,24-diol (7)

To a solution of 3.0 g (5.1 mmol) of (6) in dry tetrahydrofuran (250 ml) was added 3.6 g (0.09 mol) of lithium aluminum hydride. The mixture was heated under reflux for 3 hrs., cooled with ice water bath and reaction mixture decomposed by the cautious dropwise addition of ice water (5 ml). The mixture was filtered and the filtrate was concentrated in vacuo to remove most of the tetrahydrofuran. The residue was dissolved in 200 ml of ethyl acetate and washed twice with saturated NaCl solution (2×200 ml), dried over anhydrous $MgSO_4$ and concentrated in vacuo. The residue was purified on a silica gel column using 30% ethyl acetate in hexane to yield 1.5 g (71%) of (7).

$^1$H NMR: (400 MHZ, $CDCl_3$): δppm 0.64 (3H, s, 18-H), 0.88 (6H, dd, 26 and 27-$CH_3$), 0.93 (3H, s, 19-$CH_3$), 1.06 (3H, d, 21-$CH_3$), 1.19 (3H, s, 28-$CH_3$), 3.55 (1H, m, 3α-H), 5.36 (1H, d, 7-H), 5.42 (2H, m, 22 and 23-H), 5.52 (1H, d, 6-H). UV (ethanol) $\lambda_{max}$: 282 nm.

24-hydroxyvitamin $D_2$ (8)

One gram (2.4 mmol) of (7) was dissolved in 250 ml of ether and benzene (4:1) and irradiated with stirring under nitrogen in a water-cooled quartz immersion well using a Hanovia medium-pressure UV lamp for 2 hrs. The solution was concentrated in vacuo, redissolved in 100 ml of ethanol and heated under reflux overnight. The solution was concentrated to dryness in vacuo and the residue was purified on a silica gel column using 30% ethyl acetate in hexane to yield 0.55 g (55%) of (8).

$^1$H NMR: (400 MHZ, $CDCl_3$): βppm 0.57 (3H, s, 18-$CH_3$), 0.92 (6H, dd, 26 and 27-$CH_3$), 1.06 (3H, d, 21-$CH_3$), 1.20 (3H, s, 28-$CH_3$), 3.93 (1H, m, 3-H), 4.79 (1H, m (sharp), 19-H), 5.01 (1H, m, (sharp), 19-H), 5.43 (2H, m, 22 and 23-H), 6.02 (1H, d, 7-H), 6.22 (1H, d, 6-H). UV (ethanol) $\lambda_{max}$: 265 nm.

EXAMPLE 2

Synthesis of 24(S)-hydroxyvitamin $D_2$ (9) [24(S)-OH-$D_2$]

Product (8) is subjected to high pressure liquid chromatography (HPLC) on Zorbax-SIL developed with hexane/isopropanol/methanol (91:7:2) or using a reverse-phase Supelco C-8 prep. column (25 cm×21.2 mm; particle size 12 μm) with the solvent system, acetonitrile:water, 60:40, 10 mL/min. The diastereomers (9) and (10) are eluted, and thereby, separated.

Figure 3:
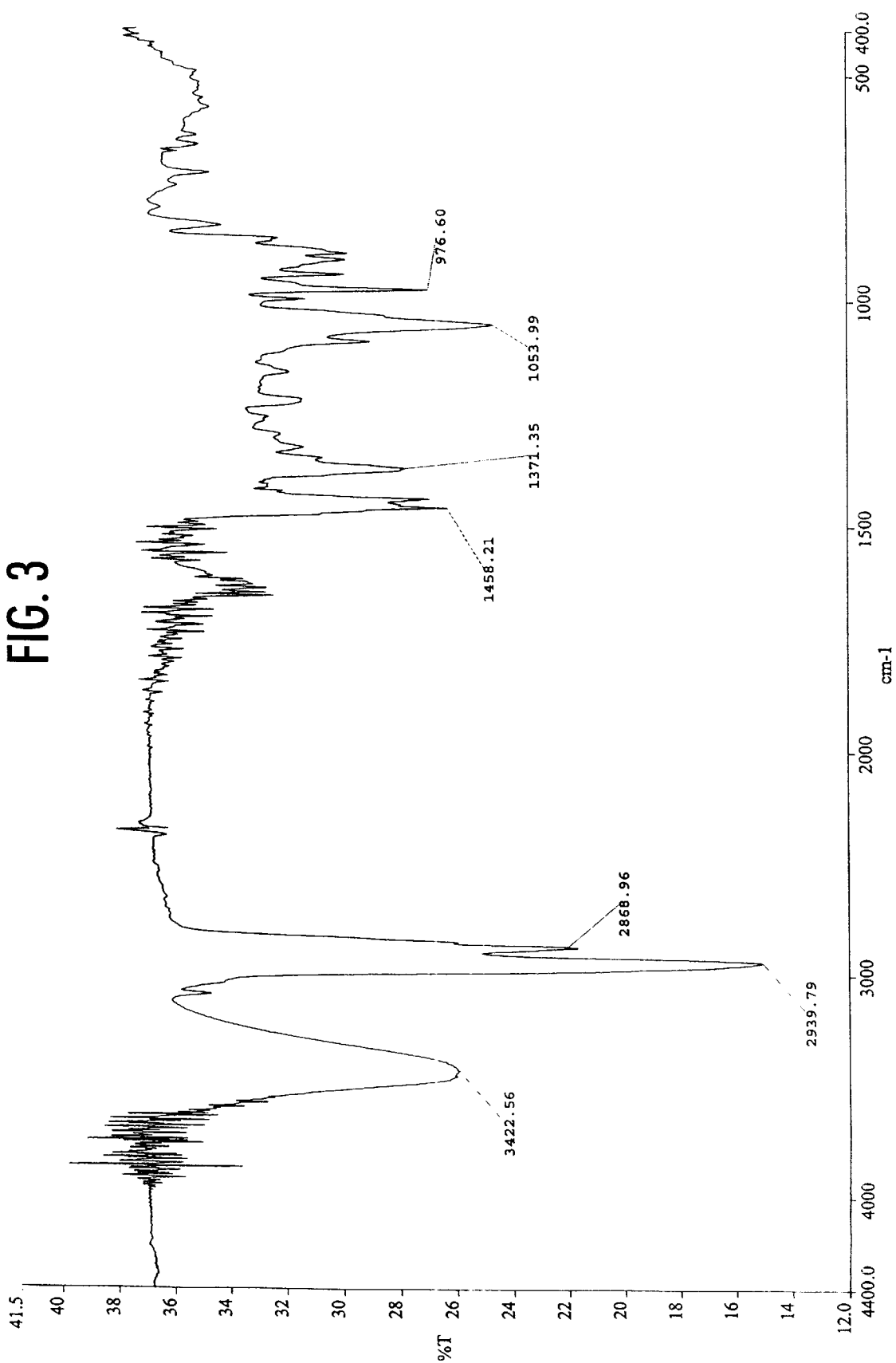
FIG. 3 is an IR spectrum of 24(S)-hydroxyvitamin $D_2$.
Figure 4:
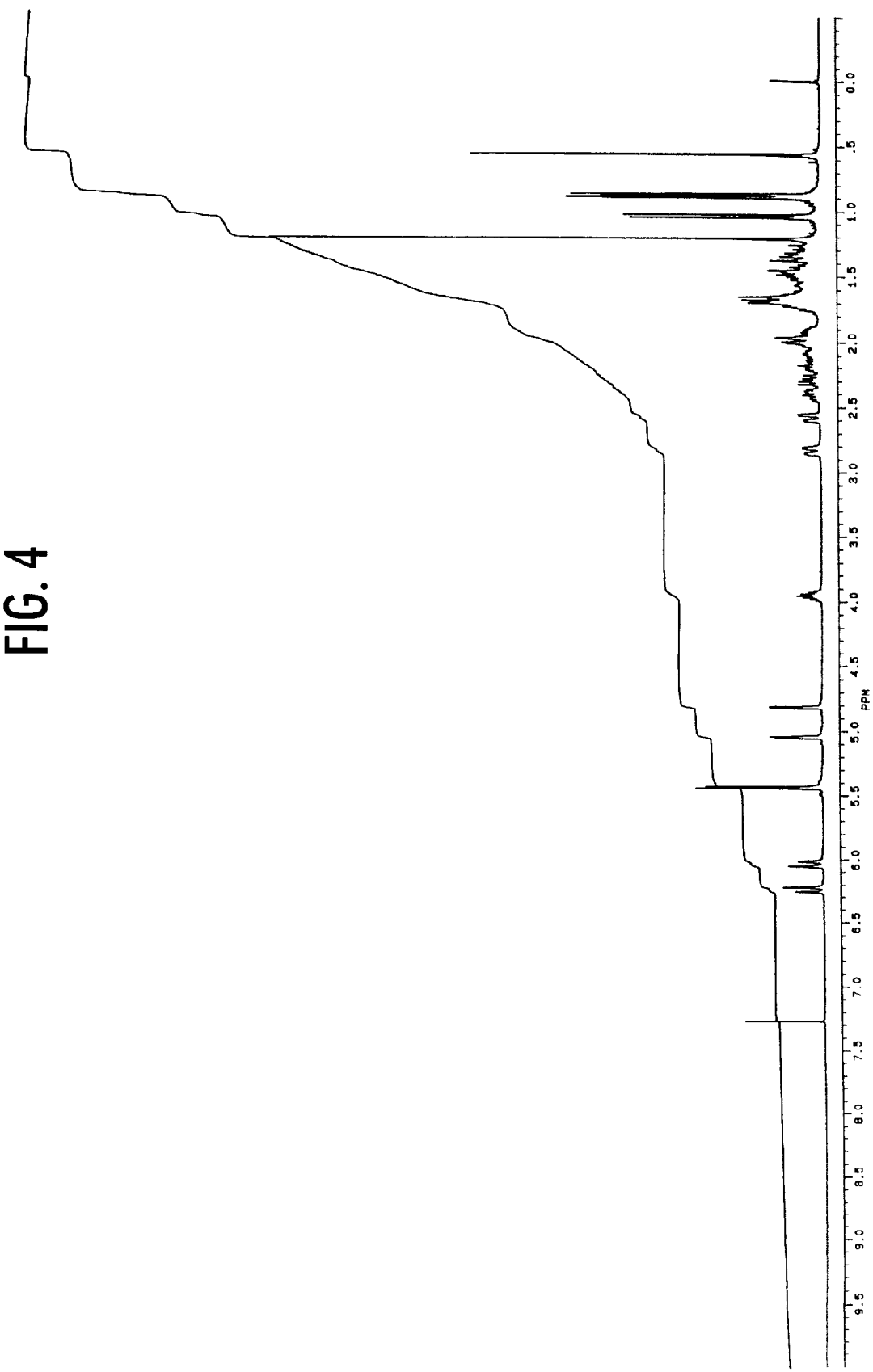
FIG. 4 is an NMR spectrum of the compound of FIG. 3.

24(S)-Hydroxyvitamin $D_2$ was characterized as follows: optical rotation: $[\alpha]_D^{24.0° C.}$=+120.4 (c=1.0, ethanol); m.p.: 123–126° C.; TLC: $R_f$=0.10 (4:1, hexane, ethylacetate, silica; Whitman No. 4500-101), elemental analysis: calc'd. c=81.50, H=10.75; found c=81.62, H=10.66. An infrared spectrum (IR) (KBr) is shown in FIG. 3, and an nuclear magnetic resonance (NMR) spectrum (300 $MH_3$, $^1$H in $CDCl_3$) as given in FIG. 4.

EXAMPLE 3

In vivo generation of 1α,24(S)-dihydroxyvitamin $D_2$ [1α,24(S)-$(OH)_2$-$D_2$] from 24(S)-OH-$D_2$ 24-OH-$D_2$ was administered (either oral or intraperitoneal supplementation) to vitamin D-deficient rats. Lipid extracts of the plasma were prepared and the metabolites purified by the method of Horst et al. (Horst, R. L., Koszewski, N. J. and Reinhardt, T. A., *Biochem.*, 29:578–82 (1990) and incorporated herein by reference) described below for synthesizing standard biological 1α,24-$(OH)_2D_2$.

Standard biological 1α,24-$(OH)_2$-$D_2$ was synthesized in vitro from 24-OH-$D_2$ by incubating 10 μg of 24-OH-$D_2$ in flask containing 5 ml of 20% kidney homogenates made from vitamin D-deficient chicks. The product of this reaction was isolated by HPLC and identified by mass spectrometry. In the lipid extracts of the plasma from the vitamin D-deficient rats administered vitamin $D_2$ or 24-OH-$D_2$, one metabolite isolated co-migrated on HPLC with the standard 1α,24-$(OH)_2D_2$, indicating that 1α,24-$(OH)_2D_2$ is a natural metabolite of vitamin $D_2$. In contrast, comparable rats administered vitamin $D_3$ had no detectable 24-OH-$D_3$.

EXAMPLE 4

In vivo generation of 1α,24(S)-$(OH)_2$-$D_2$ from 24(S)-hydroxyprevitamin $D_2$ [24(S)-OH-previtamin $D_2$]

Male weanling rats are fed a diet deficient in vitamin D and with normal calcium (0.47%). After a period of four weeks has elapsed, the rats are divided into two groups, and orally administered either 24-OH-previtamin $D_2$ (0.25 μg/kg) in a vehicle such as lactose or the vehicle (control) alone. Four hours after administration, the rats are killed and their blood level of 1α,24-$(OH)_2$-$D_2$ is measured using a standard technique.

Following this procedure demonstrates that the blood level of 1α,24-$(OH)_2$-$D_2$ is significantly elevated over the blood level of control animals.

EXAMPLE 5

Production of 1α,24(S)-dihydroxy-25-ene-vitamin $D_2$ [1α,24(S)-$(OH)_2$-25-ene-$D_2$] in osteoporotic women administered 24-(OH)-25-ene-$D_2$.

Human female subjects, who have been diagnosed with osteoporosis, are given daily doses of 25 μg/day 24-OH-25-ene-$D_2$ for one week. Blood is collected and analyzed for the metabolite 1α,24(S)-$(OH)_2$-25-ene-$D_2$. Lipid is extracted from the blood, and the metabolite is purified by HPLC using standard methods and quantified with the radioreceptor assay produced by lncstar (Stillwater, Minn.). One day following the last dose of 25 μg, the results show that there is a significant level of 1α,24(S)-$(OH)_2$-25-ene-$D_2$ in the blood.

EXAMPLE 6

Treatment of osteoporosis with 24(S)-OH-pre$D_2$

A clinical study is conducted with postmenopausal osteoporotic outpatients having ages between 55 and 75 years. The study involves up to 120 patients randomly divided into three treatment groups, and continues for 24 months. Two of the treatment groups receive constant dosages of orally administered 24-OH-pre$D_2$ (u.i.d.; two different dose levels above 5.0 μg/day) and the other group receives a matching placebo. All patients maintain a normal intake of dietary calcium (500 to 800 mg/day) and refrain from using calcium supplements. Efficacy is evaluated by pretreatment and posttreatment comparisons of the patient groups with regard to (a) total body, radial, femoral, and/or spinal bone mineral density as determined by x-ray absorptiometry (DEXA), (b) bone biopsies of the iliac crest, and (c) determinations of serum osteocalcin. Safety is evaluated by comparisons of urinary hydroxyproline excretion, serum and urine calcium levels, creatinine clearance, blood urea nitrogen, and other routine determinations.

This study demonstrates that patients treated with orally administered 24-OH-pre$D_2$ exhibit significantly higher total body, radial, femoral, and/or spinal bone densities relative to patients treated with placebo. The treated patients also exhibit significant elevations in serum osteocalcin. Bone biopsies from the treated patients show that 24-OH-pre$D_2$ stimulates normal bone formation. The monitored safety parameters confirm an insignificant incidence of hypercalcemia or hypercalciuria, or any other metabolic disturbance with 24-OH-pre$D_2$.

EXAMPLE 7

Preventive treatment of bone mass loss in postmenopausal osteoporotic women using 24(S)-OH-25-ene-$D_2$ A clinical study is conducted with postmenopausal osteoporotic out-patients having ages between 55 and 75 years. The study involves up to 120 patients randomly divided into three treatment groups and continues for 24 to 36 months. Two of the treatment groups receive constant dosages of 24(S)-OH-25-ene-$D_2$ (u.i.d.; two different dose levels at or above 5.0 µg/day) and the other group receives a matching placebo. All patients maintain a normal intake of dietary calcium (500 to 800 mg/day) and refrain from using calcium supplements. Efficacy is evaluated by pre-and post-treatment comparisons of the patient groups with regard to (a) total body calcium retention, and (b) radial and spinal bone mineral density as determined by dual-photon absorptiometry (DPA) or dual-energy x-ray absorptiometry (DEXA). Safety is evaluated by comparisons of urinary hydroxyproline excretion, serum and urine calcium levels, creatinine clearance, blood urea nitrogen, and other routine determinations.

The results show that patients treated with 24(S)-OH-25-ene-$D_2$ exhibit significantly higher total body calcium, and radial and spinal bone densities relative to patients treated with placebo. The monitored safety parameters confirm an insignificant incidence of hypercalcemia or hypercalciuria, or any other metabolic disturbance with 24(S)-OH-25-ene-$D_2$ therapy.

EXAMPLE 8

Treatment of psoriasis with 24-OH-$D_2$

An oral dosage formulation containing 24-OH-$D_2$ is evaluated in a double blind study for therapeutic efficacy of the formulation in the treatment of dermatitis (contact and ectopic). The formulation evaluated contains 10.0 to 20.0 µg of 24-OH-$D_2$. The control formulation is identical except that it does not contain the 24-OH-$D_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing, and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, backgound, etc.).

Evaluations of erythema, scaling, and thickness are conducted at weekly intervals by a physician. The final evaluation is usually carried out at the end of four to six weeks of treatment. The results of the study show that daily oral administration of 24-OH-$D_2$ significantly reduces the degree of erythema, scaling, and thickness versus the control patients.

EXAMPLE 9

Treatment of psoriasis with 24(S)-OH-pre$D_2$

An oral dosage formulation containing 24(S)-OH-pre$D_2$ is evaluated in a double blind study for therapeutic efficacy of the formulation in the treatment of dermatitis (contact and ectopic). The formulation evaluated contains 10.0 to 20.0 µg of 24(S)-OH-pre$D_2$. The control formulation is identical except that it does not contain the 24(S)-OH-pre$D_2$. The patients are treated in an outpatient clinic and are divided into an experimental and control population. They are instructed to take the medication once a day, in the morning before breakfast.

In each patient (experimental and control) an area of the skin containing a lesion is selected which is ordinarily covered by clothing, and the patients are instructed not to expose the skin area selected for study to sunlight. The area of the lesion is estimated and recorded, and the lesion(s) is photographed. Relevant details of the photographic procedure are recorded so as to be reproduced when the lesions are next photographed (distance, aperture, angle, backgound, etc.).

Evaluations of erythema, scaling, and thickness are conducted at weekly intervals by a physician. The final evaluation is usually carried out at the end of four to six weeks of treatment. The results of the study show that daily oral administration of 24(S)-OH-pre$D_2$ significantly reduces the degree of erythema, scaling, and thickness versus the control patients.

EXAMPLE 10

Treatment of prostate cancer using 24-(OH)-$D_2$

Patients with advanced androgen-independent prostate cancer participate in an open-label study of 24-(OH)-$D_2$. Qualified patients are at least 40 years old, exhibit histologic evidence of adenocarcinoma of the prostate, and present with progressive disease which had previously responded to hormonal intervention(s). On admission to the study, patients begin a course of therapy with oral 24-(OH)-$D_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral 24-(OH)$D_2$ is determined by administering progressively higher dosages to successive groups of patients. All doses are administered in the morning before breakfast. The first group of patients is treated with 25.0 µg of 24-(OH)$D_2$. Subsequent groups of patients are treated with 50.0, 75.0 and 100.0 µg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 µg.

Results from the first phase of the study show that the MTD for 24-(OH)$D_2$ is above 25.0 µg/day, a level which is 10- to 50-fold higher than can be achieved with $1\alpha,25$-$(OH)_2$ $D_3$. Analysis of blood samples collected at regular intervals from the participating patients reveal that the levels of circulating 24-(OH)$D_2$ increase proportionately with the dosage administered, rising to maximum levels well above 100 pg/mL at the highest dosages, and that circulating levels of $1\alpha,25$-$(OH)_2D_3$ are suppressed, often to undetectable levels. Serum and urine calcium are elevated in a dose responsive manner. Patients treated with the MTD of 24-(OH)$D_2$ for at least six months report that bone pain associated with metastatic disease is significantly diminished.

During the second phase, patients are treated with 24-(OH)$D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 11

Treatment of prostate cancer using 24-OH-preD$_2$

The study of Example 10 is repeated for the vitamin D compound, 24-OH-preD$_2$. The results of the phase one study indicate that patients treated with the MTD of 24-OH-preD$_2$ for at least six months report that bone pain associated with metastatic disease is significantly diminished. The results of the phase two study indicate that after two years, CAT scans, X-rays and bone scans used for evaluating the progression of metastatic disease show stable disease or partial remission in many patients treated at the lower dosage, and stable disease and partial or complete remission in many patients treated at the higher dosage.

EXAMPLE 12

Treatment of elderly subjects with elevated blood PTH from secondary hyperparathyroidism with 24-OH-D$_4$ A twelve-month double-blind placebo-controlled clinical trial is conducted with forty subjects with secondary hyperparathyroidism. The selected subjects have ages between 60 and 100 years and have a history of secondary hyperparathyroidism. Subjects also have femoral neck osteopenia (femoral neck bone mineral density of $\leq 0.70$ g/cm$^2$).

All subjects enter a six-week control period after which the subjects are randomized into two treatment groups: one group receives a constant dosage of 15 µg/day 24-(OH)-D$_4$, and the other group receives a matching placebo. Both groups maintain a normal intake of dietary calcium without the use of calcium supplements. Efficacy is evaluated by pre- and post-treatment comparisons of the two patient groups with regard to (a) intact PTH (iPTH); (b) radial, femoral and spinal bone mineral density; and (c) bone-specific urine markers (e.g., pyridinium crosslinks). Safety is evaluated by (a) serum calcium and phosphorus, and (b) urine calcium and phosphorus.

Analysis of the clinical data show that 24-(OH)-D$_4$ significantly decreases iPTH and bone specific urine markers. Subjects treated with this compound show normal serum calcium levels and stable radial and spinal bone densities relative to baseline values. In contrast, patients treated with placebo show no reduction in iPTH and bone-specific urine markers. An insignificant incidence of hypercalcemia is observed in the treatment group.

EXAMPLE 13

Treatment of elderly subjects with elevated blood PTH from secondary hyperparathyroidism with 24-OH-preD$_2$ A twelve-month double-blind placebo-controlled clinical trial is conducted with forty subjects with secondary hyperparathyroidism. The selected subjects have ages between 60 and 100 years and have a history of secondary hyperparathyroidism. Subjects also have femoral neck osteopenia (femoral neck bone mineral density of $\leq 0.70$ g/cm$^2$).

All subjects enter a six-week control period after which the subjects are randomized into two treatment groups: one group receives a constant dosage of 15 µg/day 24-OH-preD$_2$, and the other group receives a matching placebo. Both groups maintain a normal intake of dietary calcium without the use of calcium supplements. Efficacy is evaluated by pre- and post-treatment comparisons of the two patient groups with regard to (a) intact PTH (iPTH); (b) radial, femoral and spinal bone mineral density; and (c) bone-specific urine markers (e.g., pyridinium crosslinks). Safety is evaluated by (a) serum calcium and phosphorus, and (b) urine calcium and phosphorus.

Analysis of the clinical data show that 24-OH-preD$_2$ significantly decreases iPTH and bone specific urine markers. Subjects treated with this compound show normal serum calcium levels and stable radial and spinal bone densities relative to baseline values. In contrast, patients treated with placebo show no reduction in iPTH and bone-specific urine markers. An insignificant incidence of hypercalcemia is observed in the treatment group.

EXAMPLE 14

Treatment of patients with secondary hyperparathyroidism in end stage renal disease using 24-OH-D$_2$ Thirty renal patients are enrolled in a clinical trial to study secondary hyperparathyroidism. The patients show baseline iPTH levels greater than 1000 pg/mL. An initial dose of 24-OH-D$_2$ (50 µg 3 times/week) is increased (maximum, 100 µg 3 times/week) or decreased as necessary to attain and maintain iPTH in the range of 150–300 pg/mL. After 11–12 weeks of treatment, the iPTH levels of the patients decrease to below 1000 pg/mL, and in many cases to below 500 pg/mL. There are few episodes of hypercalcemia with the patients during the study.

EXAMPLE 15

Treatment of primary hyperparathyroidism with 24-OH-preD$_2$

Twenty renal patients are enrolled in a clinical trial to study primary hyperparathyroidism. The patients show baseline iPTH levels greater than 200 pg/mL. An initial dose of 24-OH-preD$_2$ (2–4 µg/day) is increased (maximum, 10 µg/day) or decreased as necessary to attain and maintain iPTH in the normal range. After 11–12 weeks of treatment, the iPTH levels of the patients decrease to below 100 pg/mL, and in many cases to below 60 pg/mL. There are few episodes of hypercalcemia with the patients during the study.

EXAMPLE 16

Immunological testing of 24-OH-D$_2$

Female C57BL/6 mice are used between the ages of 9–12 weeks. Mice are given food and water ad libitum and are kept in a 12-hour light and 12-hour dark cycle.

A known balanced salt solution (BSS) is prepared and supplemented to 0.01 molar with HEPES buffer.

The test compound, 24-OH-D$_{21}$ is dissolved in dimethylsulfoxide at final concentrations of 0.2 or 0.4 mg per ml. When working with vitamin D compounds, conditions of reduced lighting were employed.

Mice are apportioned at 4 per group and are inoculated intraperitoneally with $3 \times 10^6$ allogeneic P815 tumor cells and the resulting cytotoxic thymus-derived lymphocyte (CTL) activity is assessed 10 days later. Mice are treated by the intraperitoneal route with 25 microliters of test compound dissolved in dimethylsulfoxide or with dimethylsulfoxide only (vehicle control). In test 1, mice are given daily treatments of 5 micrograms of 24-OH-$D_2$ per day starting one day before immunization and continuing until the day before assay. In test 2, mice are treated with 10 micrograms of 24-OH-$D_2$ only twice: on the day before immunization and on the day of immunization.

Ten days after immunization of mice with P815 cells, single spleen cell suspensions are prepared by passage of spleens through a steel mesh into BSS and are subsequently washed twice with BSS. Further manipulations of spleen cells, labeling of P815 target cells with Cr, mechanics of the assay, and the calculation of results from the CTL assay are known and described in U.S. Pat. No. 4,749,710, incorporated herein by reference. Cytotoxic T lymphocyte activity is determined individually on spleen cells from each animal in each group and the results are expressed as the mean CTL activity (as percent specific Cr release) of each group ± the standard deviation.

The results show that mice immunized with P815 cells developed substantial CTL activity within 10 days in the vehicle control groups. A statistically significant reduction in CTL activity is seen in both tests in those groups which were treated with 24-OH-$D_2$, thus documenting the immunosuppressive activity of the compound when administered to animals.

It is to be understood that although the foregoing examples detail use of specific 24-OH-D and 24-OH-preD compounds, other compounds within the scope of the claims may be readily utilized in the treatment methods of the present invention with essentially equivalent results.

In summary, the present invention provides 24-hydroxyvitamin D prodrug compounds which include 24-hydroxyprevitamin D compounds that in vivo are 1α-hydroxylated to 1,24-hydroxyvitamin D compounds. The compounds are particularly adapted to elicit significantly less hypercalcemia than dosing with similar amounts of vitamin $D_3$ compounds such as 1,25-dihydroxy vitamin $D_3$. The compounds are useful in the treatment and prevention of hyperparathyroidism, hyperproliferative diseases as well as bone depletive disorders, and immunological and inflammatory response regulation.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

What is claimed is:

1. A method of achieving an effect in a patient comprising administering an effective amount of a vitamin D compound which is a 24-hydroxyvitamin D wherein the effect is treating or preventing bone loss or bone mineral content, hyperparathyroidism, hyperproliferation, or modulating the immune and inflammatory responses, and wherein said 24-hydroxyvitamin D is a compound of formula (I):

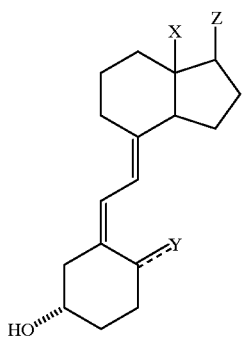

wherein Z is a side chain of formula IIC, IID, or IIE:

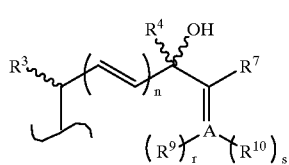

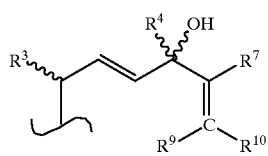

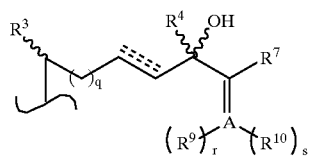

wherein a dotted line along the side chain represents an optional additional C—C bond; q is zero; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^9$ and $R^{10}$ are independently hydrogen, lower alkyl, lower alkenyl, lower fluoroalkyl or lower fluoroalkenyl; n is 1; Y is a methylene group if Y is double bonded to the A-ring or a methyl group or hydrogen if Y is single bonded; and X is hydrogen, lower alkyl or lower fluoroalkyl.

2. The method of claim 1 wherein Z is a side chain of formula (IIC).

3. The method of claim 1 wherein Z is a side chain of formula (IID).

4. The method of claim 1 wherein Z is a side chain of formula (IIE).

5. The method of claim 4 wherein said 24-hydroxyvitamin D compound is 24-OH-25-ene-$D_2$.

6. A 24-hydroxyvitamin D compound which is a compound of formula (I):

(I)

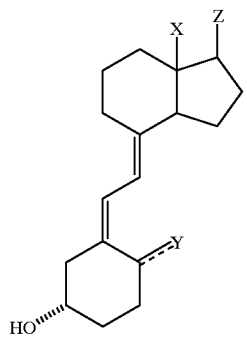

wherein Y is a methylene group if Y is double bonded to the A-ring or a methyl group or hydrogen if Y is single bonded; X is hydrogen, lower alkyl or lower fluoroalkyl; and Z is a side chain of formula (IIC):

(IIC)

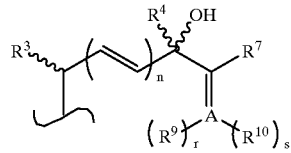

wherein n is 1; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^9$ and $R^{10}$ are independently hydrogen, lower alkyl, lower alkenyl, lower fluoroalkyl or lower fluoroalkenyl.

7. A 24-hydroxyvitamin D compound which is a compound of formula (I):

(I)

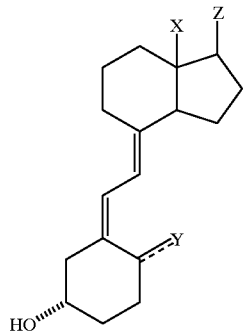

wherein Y is a methylene group if Y is double bonded to the A-ring or a methyl group or hydrogen if Y is single bonded; X is hydrogen, lower alkyl or lower fluoroalkyl; and Z is a side chain of formula (IIE):

(IIE)

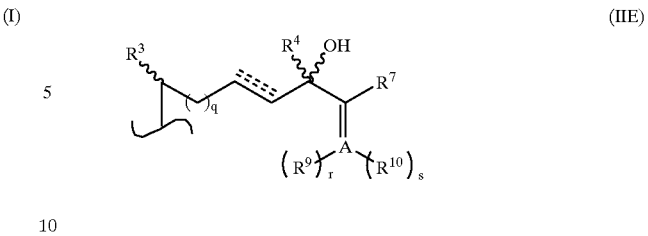

wherein a dotted line along the side chain represents an optional additional C—C bond; q is zero; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; and $R^9$ and $R^{10}$ are independently hydrogen, lower alkyl, lower alkenyl, lower fluoroalkyl or lower fluoroalkenyl.

8. A 24-hydroxyprevitamin D which is a compound of formula (III):

(III)

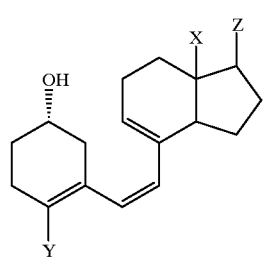

wherein Y is a methyl group or hydrogen; X is hydrogen, lower alkyl or lower fluoroalkyl; and Z is a side chain of formula (IIC):

(IIC)

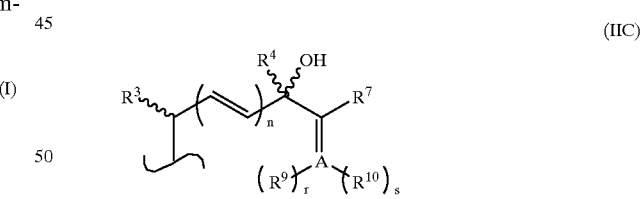

wherein n is an integer which is 1; $R^3$ is hydrogen, lower alkyl, lower fluoroalkyl, lower alkenyl or lower fluoroalkenyl, $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^9$ and $R^{10}$ are independently hydrogen, lower alkyl, lower alkenyl, lower fluoroalkyl or lower fluoroalkenyl.

9. A 24-hydroxyprevitamin D which is a compound of formula (III):

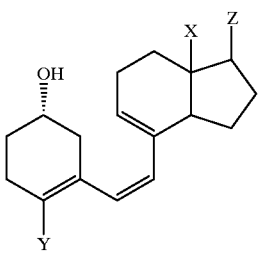

(III)

wherein Y is a methyl group or hydrogen; X is hydrogen, lower alkyl or lower fluoroalkyl; and Z is a side chain of formula (IIE):

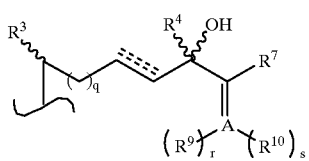

(IIE)

wherein a dotted line along the side chain represents an optional additional C—C bond; q is zero or an integer which is 1; $R^3$ is hydrogen, lower alkyl, lower fluoroalkyl, lower alkenyl or lower fluoroalkenyl; $R^4$ and $R^7$ are independently lower alkyl, lower fluoroalkyl, lower alkenyl or lower fluoroalkenyl; A is carbon, oxygen, sulfur or nitrogen; r is 1 and s is zero when A is nitrogen; r and s are 1 when A is carbon; r and s are zero when A is sulfur or oxygen; $R^9$ and $R^{10}$ are independently hydrogen, lower alkyl, lower alkenyl, lower fluoroalkyl or lower fluoroalkenyl.

10. The method of claim 1 wherein said compound is administered in combination with a bone agent, a cytotoxic agent, an immune response regulating agent, an antiinflammatory agent or combinations thereof.

11. The method of claim 10 wherein said bone agent is other vitamin D compounds, conjugated estrogens, sodium fluorides, biphosphonates, cobalamin, calcium receptor agonists, pertussin toxin, boron or DHEA.

12. The compound of claim 8 in a pharmaceutical composition including a pharmaceutically acceptable carrier, adjuvant or vehicle, wherein the composition is further combined with effective amounts of a bone agent, a cytotoxic agent, an immune response regulating agent, an antiinflammatory agent or combinations thereof.

13. The compound of claim 7 in a pharmaceutical composition including a pharmaceutically acceptable carrier, adjuvant or vehicle, wherein the composition is further combined with a bone agent, a cytotoxic agent, an immune response regulating agent, an antiinflammatory agent or combinations thereof.

14. The compound of claim 6 in a pharmaceutical composition including a pharmaceutically acceptable carrier, adjuvant or vehicle, wherein the composition is further combined with a bone agent, a cytotoxic agent, an immune response regulating agent, an antiinflammatory agent or combinations thereof.

* * * * *

UNITED STATES PATENT AND TRADEMARK OFFICE
CERTIFICATE OF CORRECTION

PATENT NO. : 6,242,434 B1
DATED : June 5, 2001
INVENTOR(S) : Charles W. Bishop et al.

It is certified that error appears in the above-identified patent and that said Letters Patent is hereby corrected as shown below:

Title page,
Item [56], References Cited, U.S. PATENT DOCUMENTS, please add the following documents:
--      5,707,980   *    1/1998  Knutson et al. …………..514/167
        5,602,116   *    2/1997  Knutson et al. …………..514/167
        5,869,473   *    2/1999  Knutson et al. …………..514/167 --.

Column 1,
Line 10, please insert before "BACKGROUND OF THE INVENTION":

-- STATEMENT REGARDING FEDERALLY SPONSORED
RESEARCH OR DEVELOPMENT

Not Applicable --.

Column 2,
Line 2, "*EndocrinoL*" should read -- Endocrinol. --.

Column 4,
Line 26, after "relates", please insert -- to --.

Column 7,
Line 57, "[24-(OH)-25F-$D_2$]" should read -- [24-(OH)-25-F-$D_2$] --.

Column 12,
Line 47, "Bisphosphonates (μg/day)" should read -- Bisphosphonates (mg/day) --.

Column 20,
Line 58, "24-OH-$D_{21}$" should read -- 24-OH-$D_2$, --.

UNITED STATES PATENT AND TRADEMARK OFFICE
CERTIFICATE OF CORRECTION

PATENT NO. : 6,242,434 B1
DATED : June 5, 2001
INVENTOR(S) : Charles W. Bishop et al.

It is certified that error appears in the above-identified patent and that said Letters Patent is hereby corrected as shown below:

<u>Column 24,</u>
Line 55, after "1", please insert -- or 2 --.

<u>Column 25,</u>
Line 28, after "1", please insert -- or 2 --.

Signed and Sealed this

Eighth Day of October, 2002

Attest:

Attesting Officer

JAMES E. ROGAN
*Director of the United States Patent and Trademark Office*